I *US012040076B2*

(12) United States Patent
Chen et al.

(10) Patent No.: US 12,040,076 B2
(45) Date of Patent: Jul. 16, 2024

(54) AUTOMATIC MYOCARDIAL ANEURYSM ASSESSMENT

(71) Applicant: Shanghai United Imaging Intelligence Co., Ltd., Shanghai (CN)

(72) Inventors: Xiao Chen, Cambridge, MA (US); Shanhui Sun, Lexington, MA (US); Terrence Chen, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 351 days.

(21) Appl. No.: 17/550,594

(22) Filed: Dec. 14, 2021

(65) Prior Publication Data
US 2023/0187052 A1 Jun. 15, 2023

(51) Int. Cl.
*G16H 30/20* (2018.01)
*A61B 5/00* (2006.01)
*A61B 5/055* (2006.01)
*G06T 7/00* (2017.01)
*G06T 7/60* (2017.01)

(52) U.S. Cl.
CPC ........... *G16H 30/20* (2018.01); *A61B 5/0044* (2013.01); *A61B 5/055* (2013.01); *G06T 7/0014* (2013.01); *G06T 7/60* (2013.01); *A61B 2576/023* (2013.01); *G06T 2207/10088* (2013.01); *G06T 2207/20081* (2013.01); *G06T 2207/20084* (2013.01); *G06T 2207/30048* (2013.01)

(58) Field of Classification Search
CPC ........ G16H 30/20; G16H 50/30; G16H 50/70; G16H 30/40; G16H 50/20; A61B 5/7267; A61B 5/0044; A61B 5/055; A61B 2576/023; G06T 7/0014; G06T 7/60; G06T 2207/10088; G06T 2207/20081; G06T 2207/20084; G06T 2207/30048
USPC ......................................... 382/268
See application file for complete search history.

(56) References Cited

U.S. PATENT DOCUMENTS

| | | | | |
|---|---|---|---|---|
| 2018/0192916 | A1* | 7/2018 | De Man | A61B 5/02007 |
| 2019/0200893 | A1* | 7/2019 | Grouchy | G06T 3/4007 |
| 2020/0155082 | A1* | 5/2020 | Maffessanti | G16H 20/40 |
| 2020/0383584 | A1* | 12/2020 | Osman | A61B 5/0044 |
| 2021/0015373 | A1* | 1/2021 | Smiricinschi | A61B 5/0263 |
| 2021/0353171 | A1* | 11/2021 | Osman | G16H 40/63 |
| 2022/0125324 | A1* | 4/2022 | Berson | A61B 5/7264 |
| 2022/0151567 | A1* | 5/2022 | Chitiboi | A61B 5/7264 |

* cited by examiner

*Primary Examiner* — Michael Robert Cammarata
*Assistant Examiner* — Pardis Sohraby
(74) *Attorney, Agent, or Firm* — Zhong Law LLC

(57) ABSTRACT

Described herein are systems, methods and instrumentalities associated with automatic assessment of aneurysms. An automatic aneurysm assessment system or apparatus may be configured to obtain, e.g., using a pre-trained artificial neural network, strain values associated one or more locations of a human heart and one or more cardiac phases of the human heart and derive a representation (e.g., a 2D matrix) of the strain values across time and/or space. The system or apparatus may determine, based on the derived representation of the strain values, respective strain patterns associated with the one or more locations of the human heart and further determine whether the one or more locations are aneurysm locations by comparing the automatically determined strain patterns with predetermined normal strain patterns of the heart and determining the presence or risk of aneurysms based on the comparison.

16 Claims, 8 Drawing Sheets

AUTOMATIC MYOCARDIAL ANEURYSM ASSESSMENT

BACKGROUND

Myocardial aneurysms such as ventricular aneurysms can cause serious health problems including, for example, a complete occlusion of the left anterior descending artery. Currently, the diagnosis and assessment of myocardial aneurysm are performed manually. Medical images such as cardiac magnetic resonance (CMR) images may be acquired and a medical professional may determine the presence of aneurysms by observing the structure and dynamics of the myocardium in the medical images. For instance, a ventricular muscle may bulge in areas where aneurysms are present and those areas may also appear dyskinetic through a cardiac contraction and relaxation cycle. The observer may manually contour these areas and further determine the severity of the aneurysms based on the contour. The process is time consuming and the accuracy of the assessment depends highly on the observer's training and experience. Accordingly, systems, methods, and instrumentalities capable of automatically determining the presence and/or extent of aneurysms are highly desirable.

SUMMARY

Described herein are systems, methods, and instrumentalities associated with automatic assessment of aneurysms. An aneurysm assessment apparatus in accordance with one or more embodiments described herein may include one or more processors configured to obtain strain values associated one or more locations of a human heart and one or more cardiac phases of the human heart, derive a representation of the strain values across the one or more locations and the one or more cardiac phases, determine, based on the derived representation of the strain values, respective strain patterns associated with the one or more locations of the human heart, and determine, based on the respective strain patterns, whether the one or more locations are aneurysm locations. In examples, the strain values obtained by the aneurysm assessment apparatus may be represented with one or more strain maps such as one or more high spatial resolution strain maps that indicate pixel-wise strain values of the human heart. In examples, the strain values may be determined by the aneurysm assessment apparatus using an artificial neural network. In other examples, the strain values may be received by the aneurysm assessment apparatus from another apparatus or from a medical data repository.

In examples, the aneurysm assessment apparatus may be configured to determine the presence of aneurysms by comparing the respective strain patterns associated with the one or more locations of the human heart with corresponding predetermined normal strain patterns associated with the one or more locations of the human heart and determining whether the one or more locations are aneurysm locations (e.g., having a high probability of being aneurysm locations) based on the comparison. In examples, the representation of the strain values described above may include a two-dimensional (2D) matrix across time and space and the aneurysm assessment apparatus may be configured to extract the respective strain patterns associated with the one or more locations of the human heart from the 2D matrix using at least one of a principal component analysis (PCA) technique or a machine learning technique (e.g., random forest, deep learning, etc.). In examples, the respective strain patterns associated with the one or more locations of the human heart may include respective average strain values at the one or more locations of the human heart across the one or more cardiac phases, and wherein the aneurysm assessment apparatus may be configured to determine whether the one or more locations are aneurysm locations by comparing the respective average strain values at the one or more locations of the human heart with predetermined normal average strain values for the one or more locations of the human heart and determining whether the one or more locations are aneurysm locations based on the comparison.

In examples, for each of the one or more locations that is determined to be an aneurysm location, the aneurysm assessment apparatus may be further configured to determine a respective segment of the human heart to which the aneurysm location belongs, determine an aneurysm size based on a number of pixels associated with the aneurysm location, determine a segment size based on a number of pixels associated with the segment, and determine whether the segment is an aneurysm segment based on a ratio of the aneurysm size to the segment size. In examples, the aneurysm assessment apparatus may be configured to determine whether a segment of the human heart is an aneurysm segment by comparing the ratio of the aneurysm size to the segment size with a configurable threshold and determining whether the segment is the aneurysm segment based on the comparison. In examples, for each of the one or more locations that is determined to be an aneurysm location, the aneurysm assessment apparatus may be further configured to indicate the aneurysm location on a strain map and overlay the strain map with a cardiac magnetic resonance (CMR) image of the human heart so as to indicate the aneurysm location with respect to the anatomy of the human heart. In examples, a strain map as described herein may be associated with a first cardiac phase and an CMR image of the human heart may be associated with a second cardiac phase. In these examples, the aneurysm assessment apparatus may be configured to overlay the strain map with the CMR image by adjusting the strain map such that coordinates of the human heart in the strain map are aligned with coordinates of the human heart in the CMR image.

BRIEF DESCRIPTION OF THE DRAWINGS

A more detailed understanding of the examples disclosed herein may be obtained from the following description, given by way of example in conjunction with the accompanying drawing.

DETAILED DESCRIPTION

The present disclosure is illustrated by way of example, and not by way of limitation, in the figures of the accompanying drawings. Embodiments may be described herein using one or more specific human anatomical structures such as the human heart (e.g., a myocardium) and/or one or more types of imagery data such as CMR images as examples. But those skilled in the art will appreciate that the techniques disclosed herein may not be limited to the example anatomical structures or the example types of imagery data. Rather, the disclosed techniques may also be used to assess aneurysms in other areas of the human body and/or based on other types of medical scan images.

Figure 1:
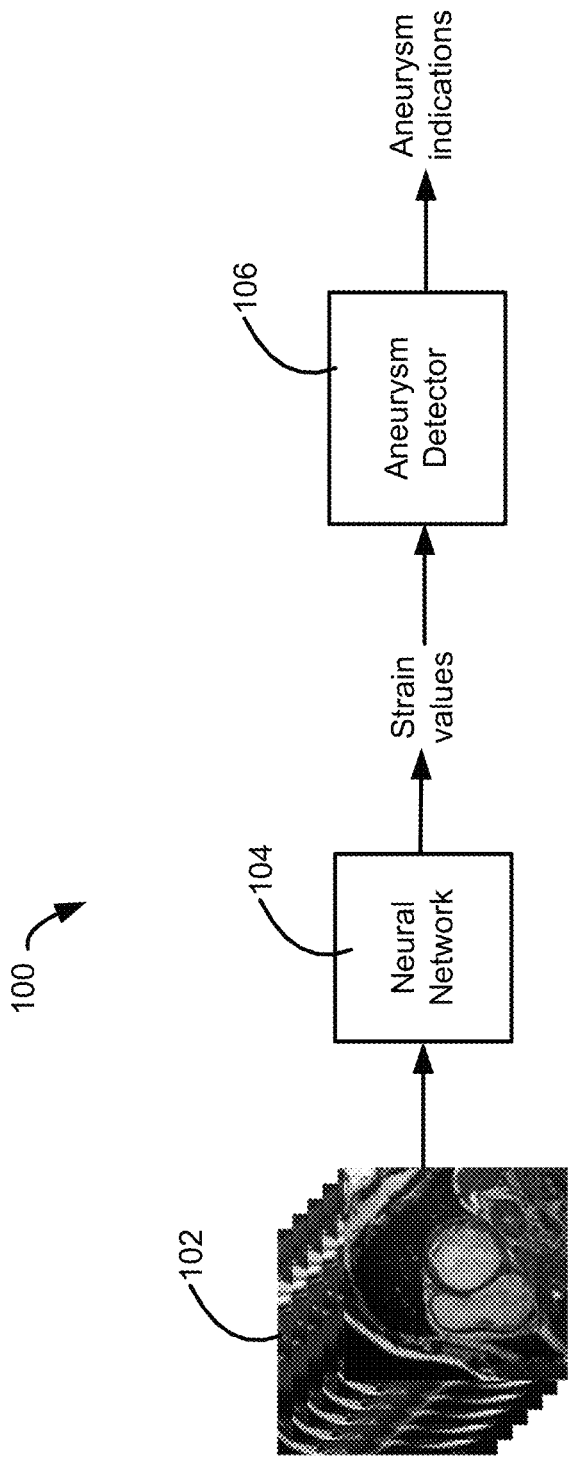
FIG. 1 is a block diagram illustrating an example of an aneurysm assessment system or apparatus in accordance with one or more embodiments described herein.

FIG. 1 is a block diagram illustrating an example aneurysm assessment system or apparatus 100 in accordance with one or more embodiments described herein. As shown, aneurysm assessment system 100 may be configured to determine the presence of aneurysms in a human heart based on medical scan images of the heart such as cardiac magnetic resonance (CMR) images 102 of the heart. CMR images 102 may be obtained, for example, from a cardiac cine movie and may include short-axis and/or long-axis MR images of the heart, 2-chamber MR images of the heart, 3-chamber MR images of the heart, etc. Aneurysm assessment system 100 may include one or more artificial neural networks (ANNs) 104 trained to determine, based on CMR images 102, structural and/or kinetic information of the heart that may be indicative of the presence of aneurysms. The structural information may include, for example, the thickness of the myocardium while the kinetic information may include, for example, strain values associated with one or more locations of the heart and/or one or more cardiac phases of the heart. When referred to herein, strains or strain values may include any metrics (e.g., change ratios, etc.) that may be used to measure the deformation of a human heart such as the deformation of a myocardium (e.g., shortening, thickening, and/or lengthening of the myocardium). The one or more locations described above may be associated with respective segments in the standard American Heart Association (AHA) cardiac segmentation model (e.g., which segments the myocardium into 17 segments), and the one or more cardiac phases described above may include atrial contraction, isovolumetric contraction, rapid ejection, reduced ejection, isovolumetric relaxation, rapid filling, and/or reduced filling, which may be further grouped into a diastole phase and a systole phase. In examples, the strain values determined using ANN 104 may include pixel-wise strain values (e.g., a strain value is obtained for each pixel of CMR image 102) and the strain value may be represented by one or more high spatial resolution strain maps (e.g., heat maps indicating pixel-wise strain values in each frame of a cine movie). In other examples, the strain values determined using ANN 104 may have other spatial resolutions (e.g., per region, per transmural layer, etc.) and/or may be represented in other forms including, for example, line graphs, tables, etc.

The strain values determined by ANN 104 may be indicative of the presence of abnormal heart conditions such as aneurysms. This is because, for example, for a normal heart tissue, when the heart contracts, circumferential strains of the tissue may decrease, radial strain of the tissue may increase, and longitudinal strains of the tissue may also decrease. For an abnormal tissue such as one at an aneurysm site, the diseased fibrotic properties of the tissue may cause the tissue to not contract properly and as a result, changes in the strains of the tissue may be minimal and/or opposite to those of a normal tissue (e.g., due to passive movements of the abnormal tissue). These abnormalities in the strain patterns of the heart may be detectable only over multiple images and, even when detected, may be imperceptible to human eyes.

Thus, aneurysm assessment system 100 may further include aneurysm detector 106 configured to receive the strain values provided by ANN 104 and automatically determine the strain patterns for one or more parts or locations of the heart. Based on these strain patterns, aneurysm detector 106 may be further configured to automatically determine whether the one or more locations of the heart are aneurysm sites or have a high probability of being aneurysm sites. For example, aneurysm detector 106 may compare the strain pattern determined for a location of the heart with a predetermined normal strain pattern of the location and determine whether the location is an aneurysm location based on the comparison. To illustrate, based on prior knowledge of the heart received by aneurysm detector 106, it may determine that a normal strain pattern of the location should show that a circumferential strain decreases first (e.g., indicating a contraction) and then increases (e.g., indicating a relaxation). If the determined strain pattern shows that the circumferential strain at the location follows the same pattern, aneurysm detector 106 may determine that the location is a normal location (e.g., having a low risk or probability of aneurysms). On the other hand, if the determined strain pattern shows that the circumferential strain increases first and then decreases, aneurysm detector 106 may determine that the location is an aneurysm location (e.g., having a high risk or probability of aneurysms).

As another example, given a set of strain values across locations and cardiac phases, aneurysm detector 106 may be configured to determine respective average strain values at the one or more locations of the heart across the one or more cardiac phases (e.g., the averages may be temporal averages) and determine whether the one or more locations are aneurysm locations by comparing the determined average strain values with predetermined normal average strain values for the one or more locations. If the determined average strain value for a location matches the predetermined normal average strain value for the location, aneurysm detector 106 may determine that the location is a normal location. If the determined average strain value for the location does not match the predetermined normal average strain value (e.g., the two values differ by a margin greater than a threshold), aneurysm detector 106 may determine that the location is an aneurysm location. As yet another example, aneurysm detector 106 may be configured to detect aneurysms based on both spatial and temporal features (e.g., based on spatial-temporal strain patterns). For instance, aneurysm detector 106 may be configured to focus on detecting the temporal strain patterns of a specific region of the heart (e.g., the apical region wherein aneurysm sites, if exist, tend to be connected to each other) and if the region exhibits dyskinetic behaviors along time, aneurysm detector 106 may determine that the region contains aneurysms or has a high risk or probability of containing aneurysms.

Aneurysm assessment system 100 (e.g., aneurysm detector 106) may be further configured to provide an indication of where aneurysms (e.g., if any is detected using the techniques described above) are located on the heart. The indication may be provided in various manners. For instance, the indication may be provided on a strain map (e.g., which may be associated with a cardiac phase) and by color-coding the strain map to indicate the aneurysmal regions and normal regions (e.g., dyskinetic or aneurysmal areas may be presented in blue while active or normal regions may be presented in red). In examples, aneurysm assessment system 100 may be further configured to overlay the color-coded strain map on top of an anatomical image (e.g., an CMR image) of the heart so as to provide a visualization of the identified aneurysms against the anatomy of the heart.

Figure 2:
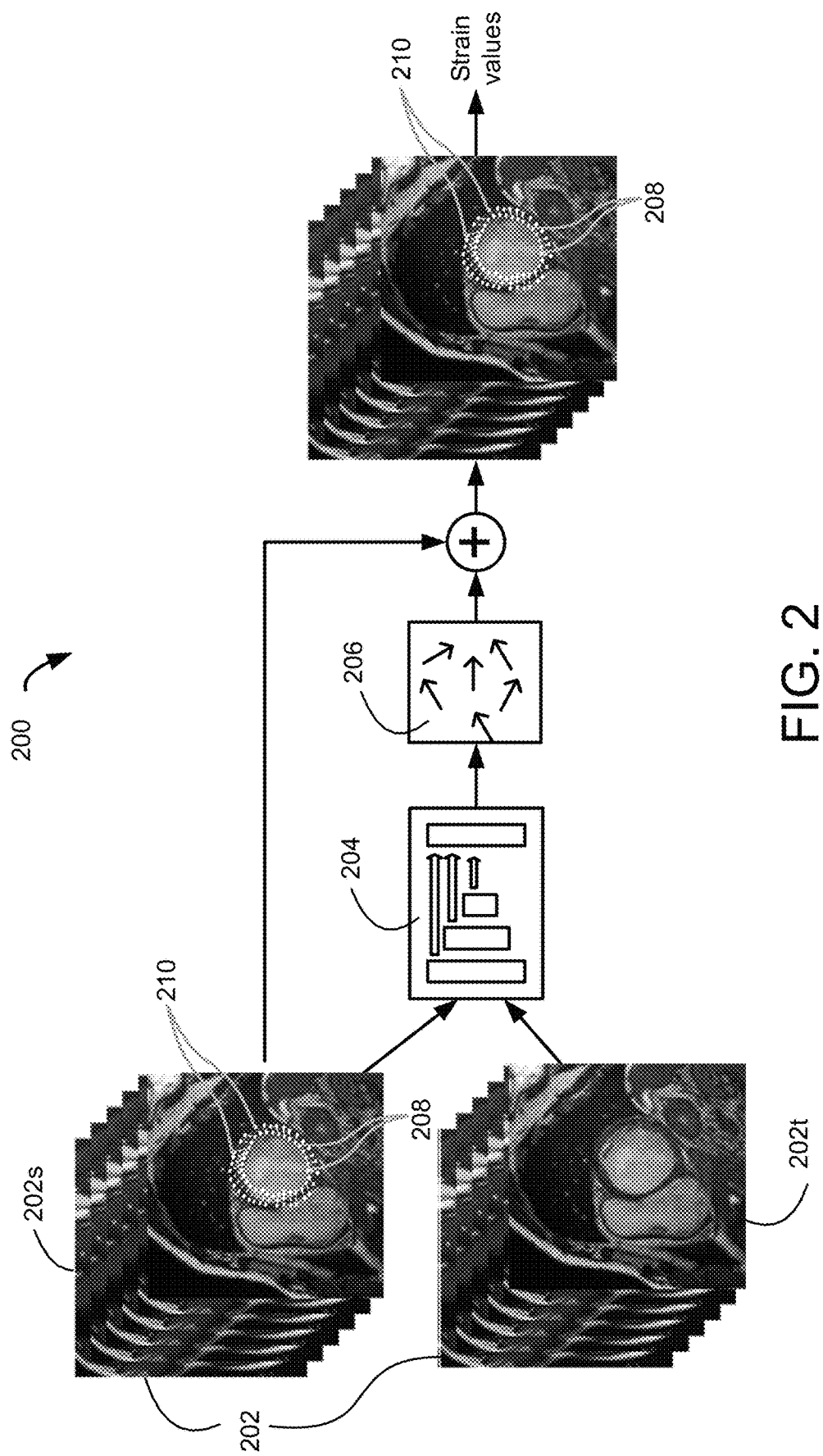
FIG. 2 is a block diagram illustrating example techniques for determining the strain values associated with a human heart in accordance with one or more embodiments described herein.

FIG. 2 is a diagram illustrating example techniques for determining the strain values associated with a human heart (e.g., the myocardium of the heart) based on MR images 202 of the heart. The example techniques may be implemented in an aneurysm assessment system or apparatus 200 (e.g., aneurysm assessment system 100 of FIG. 1) that may comprise neural network 204. As described herein, MR images 202 may be obtained from a cardiac cine movie that records the motion of the myocardium during a cardiac cycle (e.g., starting from relaxation to contraction and then back to relaxation), and each MR image 202 may correspond to a specific time within the cardiac cycle and may depict the state of the myocardium at that time. As such, neural network 204 may be trained to estimate the motion of the myocardium by extracting respective features from source image 202s and target image 202t (e.g., any two images in the cine movie), identifying changes between the two sets of features, and generating motion field 206 (e.g., a vector, a grid of vectors, a vector-value function, a map, and/or the like) to represent the changes. Neural network 204 may then treat target image 202t as a new source image, compare its features with those of another target image (e.g., another MR image in the cine movie), and represent the motion from target image 202t to the other target image with another motion field. In similarly manners, neural network 204 may repeat the operations described above for other images of the cine movie to track the motion of the myocardium throughout the cardiac cycle.

Neural network 204 may include a convolutional neural network (CNN) comprising an encoder and/or a decoder (e.g., arranged as a variational autoencoder). The encoder may include a plurality of layers such as one or more convolutional layers, one or more pooling layers and/or one or more fully connected layers. The encoder may be trained to extract respective features from source image 202s and target image 202t by performing a series of convolution and down-sampling operations on the images through the various layers of the neural network. For example, each convolutional layer of the encoder may include a plurality of convolution kernels or filters (e.g., with a kernel size of 3×3 or 5×5) configured to extract specific features from source image 202s and target image 202t. The convolution operations may be followed by batch normalization and/or linear or non-linear activation (e.g., via a rectified linear unit (ReLU) activation function), and the features extracted through the aforementioned operations (e.g., in the form of one or more feature maps or feature vectors) may be down-sampled through one or more pooling layers (e.g., using a 2×2 window and a stride of 2) to reduce the redundancy and/or dimensions of the features (e.g., by a factor of 2).

The decoder of neural network 204 may be configured to receive the respective features extracted from source image 202s and target image 204t, analyze (e.g., compare) the features, and generate motion field 206 (e.g., a flow field) to indicate changes (e.g., representative of a motion) of the myocardium from source image 202s to target image 202t. The decoder may include a plurality of layers such as one or more convolutional layers, one or more un-pooling layers, and/or one or more fully connected layers. Through these layers, the decoder may perform a series of up-sampling and/or transposed convolution (e.g., deconvolution) operations on the respective feature extracted by the encoder described above. For example, the decoder may up-sample the extracted features using the one or more un-pooling layers (e.g., based on pooling indices provided by the encoder) and the one or more convolutional layers (e.g., using 3×3 or 5×5 transposed convolutional kernels and/or a stride of 2) to obtain an up-sampled (e.g., dense) representation of the features. Based on the up-sampled features, the decoder may derive motion field 206, which may include a vector, a grid of vectors, a vector-value function, and/or the like that may indicate the disparities or displacements of features between source image 202s and target image 202t. The motion fields derived using this technique may then be used to determine the myocardial strains of the heart, for example, by conducting a finite strain analysis of the myocardium (e.g., using one or more displacement gradient tensors calculated from the motion fields).

Although motion tracking is described above with reference to an encoder, a decoder, and/or other neural network components or machine-learning techniques, it should be noted that the task may also be accomplished using other types of neural networks and/or machine-learning models. For instance, upon estimating motion field 206, the neural network may be trained to treat the motion field as a first or coarse motion field and perform additional operations to refine the motion indicated by the motion field. These additional operations may include, for example, warping source image 202s to derive a warped image based on the predicted first motion field (e.g., via spatial transformation) and determining a second motion field between the warped image and target image 202t. The second motion field may then be combined with the first motion field (e.g., by aggregating the respective motions indicated in the first and second motion fields) to obtain a refined motion field. As another example, a neural network may be trained to predict the motion field described herein based on a source segmentation mask and a target segmentation mask associated with a myocardium (e.g., the segmentation masks may be generated based on images of the myocardium using a pre-trained segmentation network). During training, the neural network may receive a source segmentation mask and a target segmentation mask, and estimate a motion field based on the segmentation masks (e.g., by comparing features extracted from the masks). The neural network may then warp the source segmentation mask (e.g., through spatial transformation) based on the motion field to obtain a warped segmentation mask, and adjust the parameters (e.g., weights) of the neural network based on a difference between the warped segmentation mask and the target segmentation mask. In yet another example, CMR images of a heart may be tagged with artificial or temporal grids that may deform with the underlying anatomical structures (e.g., components of the heart), and motion information associated with the heart may then be determined based on the displacement or deformation of the grids and used to calculate the strains. In yet another example, motion information associated with the heart may be directly encoded into a CMR image (e.g., through displacement encoding with stimulated echoes) and the displacement-encoded CMR image may subsequently be used to derive the motion information.

An example technique for determining myocardial strains will now be described with respect to FIG. 2, FIG. 3, and FIGS. 4A-4C. Those skilled in the art will appreciate, however, that various other techniques (e.g., the finite strain analysis technique described above and/or techniques based on other modalities such as ultrasound) may also be utilized to determine the strains. In the example technique, aneurysm assessment system 200 may be configured to determine (e.g., using one or more layers of neural network 204 or another component of the aneurysm assessment system) a first plurality of feature points 208 located on a first surface of the myocardium (e.g., an inner surface of the myocardium or the endocardium) and a second plurality of feature points 210 located on a second surface of the myocardium (e.g., an outer surface of the myocardium or the epicardium). Each of feature points 210 may correspond to one of feature points 208 such that a respective distance between two corresponding feature points on the two surfaces may indicate a respective thickness of the myocardium. The correspondence between feature points 208 and 210 may be indicated by the dotted lines shown in the figure, and the feature points and their correspondence may be derived using a partial differential equation such as Laplace's equation, as illustrated by FIG. 3.

Figure 3:
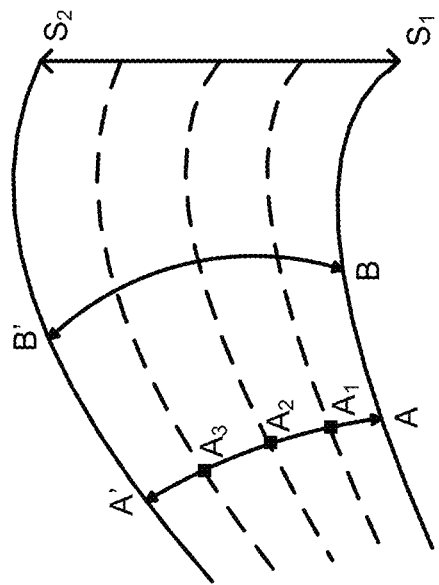
FIG. 3 is a diagram illustrating an example technique for deriving feature points on two surfaces or boundaries of a myocardium using Laplace's equation in accordance with one or more embodiments described herein.

FIG. 3 is a diagram illustrating an example technique for deriving feature points 208 and feature points 210 on two surfaces or boundaries of the myocardium using Laplace's equation. In one aspect of the technique, a scalar field $\psi$ (e.g., representing electric potential values) enclosed between two boundary contours $S_1$ and $S_2$ (e.g., an inner surface and an outer surface) of the myocardium may be the computed, for example, in accordance with the equation below:

$$\nabla^2 \psi = \frac{\delta^2 \psi}{\delta x^2} + \frac{\delta^2 \psi}{\delta y^2} + \frac{\delta^2 \psi}{\delta z^2} = 0 \qquad 1)$$

where $\psi$ may be equal to $\psi_1$ on $S_1$ and $\psi_2$ on $S_2$. By solving the equation, a layered set of surfaces (e.g., shown by the dashed lines in FIG. 2) may be determined that transition from $S_1$ to $S_2$ and respective values of $\psi$ may be defined for one or more points (e.g., any point) between the two surfaces $S_1$ and $S_2$ (e.g., A and A', B and B', etc.). Points on inner surface $S_1$ (e.g., such as points A and B) may be assigned a $\psi$ value of 0 (e.g., in units of volts to indicate an electric potential), while points on outer surface $S_2$ (e.g., such as points A' and B') may be assigned a $\psi$ value of 10,000 and points between the two surfaces (e.g., between A and A' or between B and B') may be assigned respective $\psi$ values that satisfy $\nabla^2 \psi = 0$. This way, non-intersecting (e.g., parallel) intermediate lines may be obtained based on the equation, for example, using the following formula:

$$E = -\nabla \psi \qquad 2)$$

E may be further normalized, e.g., based on the following equation, to obtain gradient vectors N that correspond to nested sublayers between $S_1$ to $S_2$:

$$N = E/\|E\| \qquad 3)$$

where N may point perpendicularly to the corresponding sublayer.

For simplicity of illustration, FIG. 3 only shows three nested sublayers (e.g., in dashed lines) that may correspond to isopotential values of 2500, 5000, and 7500V. A skilled person in the art will understand, however, that more nested sublayers may be derived in similar manners and once N is determined, a streamline may be computed by starting from a surface point (e.g., A on surface $S_1$) and integrating N (e.g., using a forward Euler integration method) to arrive at a point on the opposite surface (e.g., A' on surface $S_2$). For example, as shown in FIG. 3, a streamline may be determined to reach A' from A through interior points $A_1$, $A_2$ and $A_3$ based on a specific integration step size. And by decreasing the integration step size, more interior points between A and A' may be obtained and the accuracy of locating A' may be improved accordingly. Hence, given a point on a first surface (e.g., $S_1$ or $S_2$) of the myocardium, a corresponding point may be identified on a second surface (e.g., the opposite surface) of the myocardium by solving Laplace's equation, as described above.

Referring back to FIG. 2, since motion field 206 may indicate changes from source image 204s to target image 204t, aneurysm assessment system 200 may determine (e.g., estimate) the locations of feature points 208 and 210 in target image 202t based on motion field 206 and the locations of the feature points in source image 202s. And once the locations of feature points 208 and 210 are determined in source image 202s and target image 202t, aneurysm assessment system 200 may further calculate (e.g., using one or more layers of neural network 204 or another component of the aneurysm assessment system) strain values 212 for various parts of the myocardium.

Figure 4B:
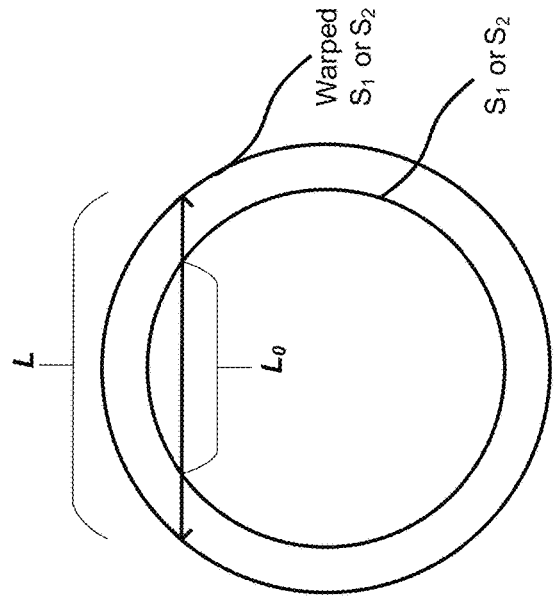
FIGS. 4A-4C illustrate example techniques for calculating strain values associated with a myocardium based on feature points located on the inner and outer surfaces of a myocardium in accordance with one or more embodiments described herein.
Figure 4A:
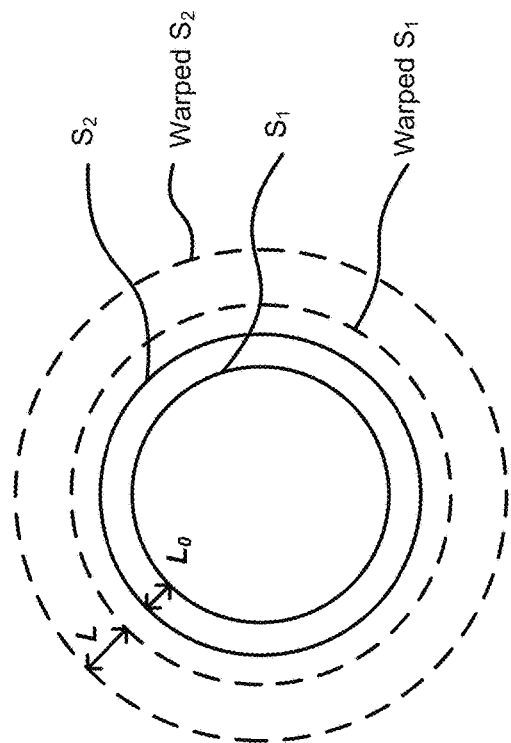

FIGS. 4A-4B illustrate example techniques for calculating strain values associated with a myocardium based on feature points (e.g., feature points 208 and 210 of FIG. 2) located on the inner and outer surfaces of the myocardium. The calculation may be performed using a strain tensor such as a Green-Lagrange tensor and/or an Engineering tensor. The strain values that may be calculated may include different types such as left ventricle (LV) radial strains, LV epicardium strains, LV endocardium strains, right ventricle (RV) strains, etc. FIG. 4A illustrates an example of calculating a radial strain. As shown, from a source MR image of the myocardium, first or initial distance $L_0$ may be determined in a radial direction of the myocardium based on two features points respectively located on inner surface $S_1$ and outer surface $S_2$ of the myocardium. One of the two feature points may be among feature points 208 shown in FIG. 2 and the other one of the two feature points may be among feature points 210 in FIG. 2. Subsequently, the two feature points used to calculate first distance $L_0$ may be identified in a target image of the myocardium and used to determine second distance L between the two feature points. Due to motions of the myocardium from the source image to the target image, surfaces $S_1$ and $S_2$ may have warped in the target image (e.g., indicated by dotted lines in FIG. 4A), so second distance L may be different than first distance $L_0$. Thus, based on the first and second distances, a radial strain of the myocardium may be determined in accordance with the following equation:

$$\varepsilon = \frac{L - L_0}{L_0} \qquad 4)$$

where distances L and $L_0$ may be represented by respective vectors.

FIG. 4B illustrates an example of calculating a circumferential strain of the myocardium. As shown, based on a source image of the myocardium, first or initial distance $L_0$ in the circumferential direction of the myocardium may be calculated, which may correspond to a projection of the radial distance between two surface points of the myocardium in the source image. The two surface points may be located on inner surface $S_1$ (e.g., an endocardium) and outer surface $S_2$ (e.g., an epicardium) of the myocardium, respectively (e.g., the surface points may be among features points 208 and 210 shown in FIG. 2). Subsequently, in a target image of the myocardium, the two surface points used to determine first distance $L_0$ may be identified and used to determine second distance L in the circumferential direction of the myocardium. Due to motions of the myocardium from the source image to the target image, surfaces $S_1$ and $S_2$ may have warped in the target image (e.g., as indicated by dotted lines in FIG. 4A), so second distance L may be different than first distance $L_0$. Thus, a circumferential strain of the myocardium may be determined using first distance $L_0$ and second distance L, for example, in accordance with Equation 4 shown above. The circumferential strain may include an endocardium circumferential strain (e.g., by projecting the radial distance onto the endocardium) representing a change in the circumferential length of the endocardium. The circumferential strain may also include an epicardium circumferential strain (e.g., by projecting the radial distance onto the epicardium) representing a change in the circumferential length of the epicardium.

Figure 4C:
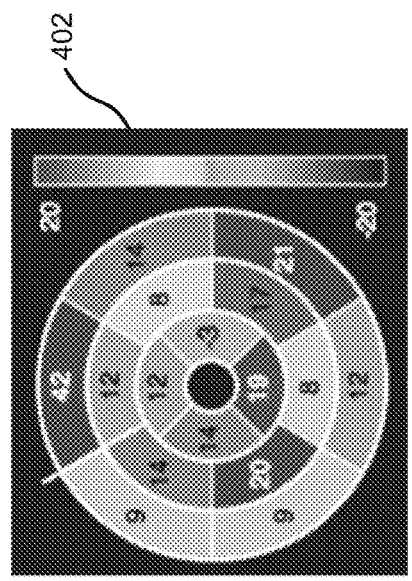

FIG. 4C illustrates an example of determining and plotting strain values for different regions of the myocardium. As shown, the myocardium may be divided into multiple (e.g., 16 or 17) segments based on AHA's cardiac segmentation model. A minimum, maximum, and/or average strain value (e.g., a radial strain and/or a circumferential strains) may be calculated for each of the segments over time (e.g., over the time period associated with an MR slice or cine movie) and the calculated value(s) may be displayed in a corresponding segment of bullseye plot 402. In examples, a value scale may also be provided (e.g., with different color-coding scheme or patterns) and plot 402 may be color-coded or patterned according to the value scale to indicate where each specific value falls within the value range. Either or both of radial and circumferential strains may be calculated and plotted. The strain values may be determined as the minimum, maximum, or average strain values of a transmural location including, for example, the endocardium, the mid-myocardium, the epicardium, etc.

Each of the neural networks described herein may include multiple layers and each of the layers may include multiple filters (e.g., kernels) with respective weights. The weights may be learned through a training process that comprises inputting a large number of images from one or more training datasets to the neural network, calculating differences or losses between a prediction result and a ground truth (e.g., based on a loss function such as MSE, L1/L2 norms, margin-based losses, etc.), and updating the weights assigned to the filters to minimize the differences or losses (e.g., based on a stochastic gradient descent of the loss function). Greater details about the neural network training process will be provided further below.

Figure 5:
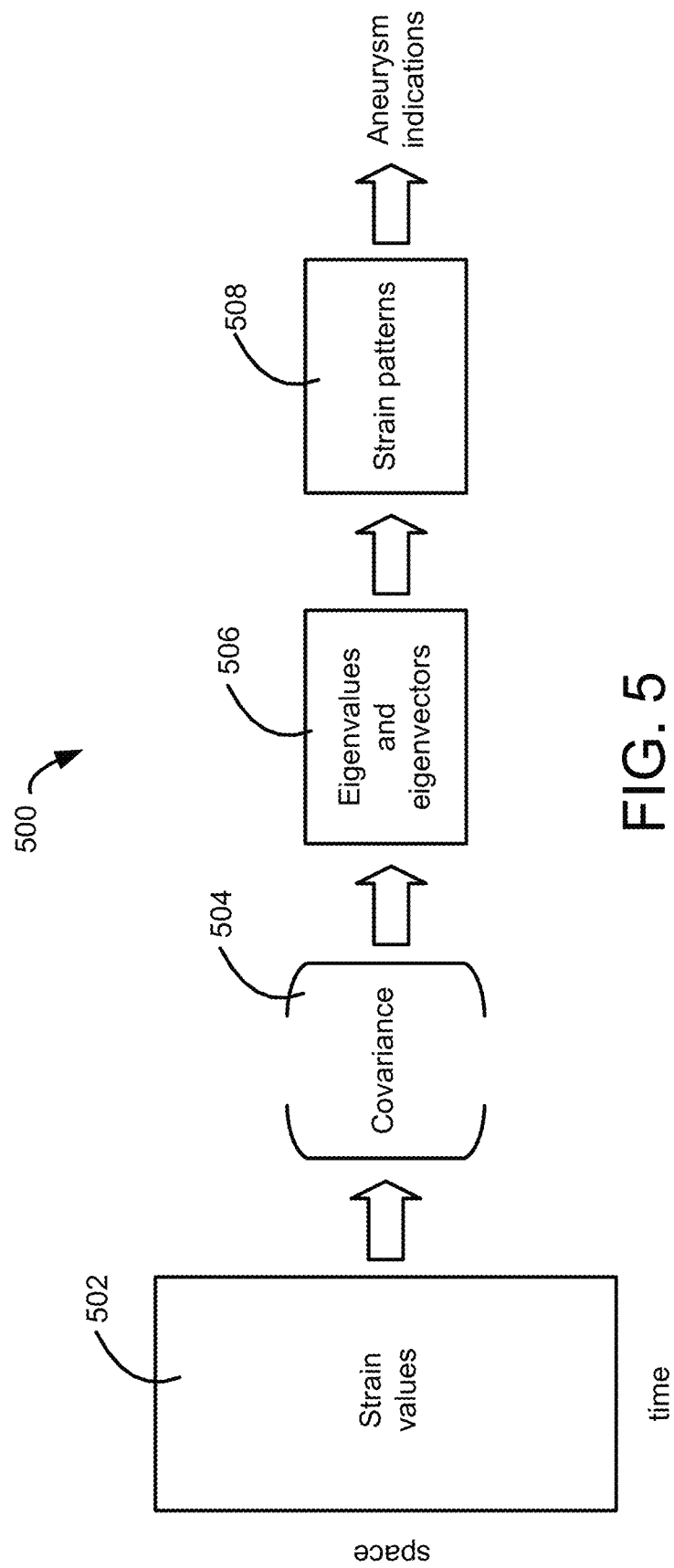
FIG. 5 a diagram illustrating example techniques for automatically identifying aneurysms in a human heart based on strain values associated with the human heart in accordance with one or more embodiments described herein.

FIG. 5 is a diagram illustrating example techniques for automatically identifying aneurysms in a human heart based on strain values associated with the human heart. The example techniques may be implemented by a system or apparatus that comprises one or more processors configured to execute computer-readable instructions for implementing the example techniques. For simplicity of description, such a system or apparatus may be referred to herein as an aneurysm detector (e.g., aneurysm detector 106 of FIG. 1). As shown in FIG. 5, aneurysm detector 500 may be configured to identify aneurysms in a human heart based on strain values 502 associated with one or more locations of the human heart and/or one or more cardiac phases of the heart. The strain values may be determined using the techniques described herein, for example, based on MR images of the heart and utilizing an artificial neural network. The artificial neural network may be a part of the same system or apparatus that implements aneurysm detector 500 or the artificial neural network may be implemented by a different system or apparatus, in which case aneurysm detector 500 may receive the strain values from the other system or apparatus or from a repository (e.g., a database, a cloud storage area, etc.) where the strain values may be saved.

Aneurysm detector 500 may obtain strain values 502 in various formats such as a strain map, a raw data file, etc. In response to obtaining strain values 502, aneurysm detector 500 may derive a representation of the strain values, for example, in the form of a multi-dimensional (e.g., two-dimensional (2D)) matrix. A first dimension of such a matrix may span across the space or locations (e.g., pixels) with which the strain values are associated, and a second dimension of the matrix may span across the time or cardiac phases (e.g., end-diastolic, end-systolic, etc.) with which the strain values are associated. Aneurysm detector 500 may analyze the derived representation to determine respective strain patterns associated with the one or more locations of the human heart. In examples, aneurysm detector 500 may conduct a principal component analysis (PCA) of representation 502 (e.g., a 2D matrix of strain values) through which aneurysm detector 500 may construct covariance matrix 504 based on the strain values included in representation 502. Aneurysm detector 500 may further derive eigenvalues and correspondent eigenvectors 506 based on covariance matrix 504, and determine respective strain patterns 508 for the one or more locations of the heart using eigenvectors 506. For instance, aneurysm detector 500 may determine strain patterns 508 for the one or more locations by projecting the original strain values associated with the locations to a space with reduced dimensions based on eigenvectors 506. In other examples, aneurysm detector 500 may determine respective strain patterns 508 for the one or more locations of the heart by calculating respective average strain values at the one or more locations across the one or more cardiac phases (e.g., each average may be calculated as a temporal average across along the time of the 2D matrix).

Upon obtaining the respective strain patterns for the one or more locations of the heart, aneurysm detector 500 may compare the obtained patterns with predetermined normal strain patterns of the one or more locations to determine whether the locations contain aneurysms (e.g., having a high risk or probability of being aneurysmal). For example, a normal strain pattern of the heart determined or received by aneurysm detector 500 may indicate that a circumferential strain at a location during a cardiac cycle decreases first (e.g., indicating a contraction) and then increases (e.g., indicating a relaxation). If the strain pattern of the location determined by aneurysm detector 500 via PCA shows that the circumferential strain follows the same pattern, aneurysm detector 500 may determine that the location is a normal location (e.g., having a low risk or probability of being aneurysmal). On the other hand, if the strain pattern determined via PCA shows that the circumferential strain increases first and then decreases, aneurysm detector 500 may determine that the location is an aneurysm location. As another example, aneurysm detector 500 may determine the average strain value (e.g., a temporal average) at a location based on the original strain values associated with the location, compare the average with a predetermined normal average strain value (or a normal value range) for the location, and determine whether the location contains aneurysms (e.g., having a high risk or probability of being aneurysmal) based on the comparison. For instance, if the determined average strain value matches the predetermined normal average (or within the normal value range) for the location, aneurysm detector 500 may determine that the location is a normal location. If the determined average strain value for the location does not match the predetermined normal average strain value (or is outside of the normal value range), aneurysm detector 500 may determine that the location is an aneurysm location.

It should be noted here that the techniques described above (e.g., using PCA and/or predetermined patterns) are only meant to show examples ways for determining abnormal strain patterns that may be indicative of aneurysms. Aneurysm detector 500 may also adopt other techniques for determining the strain patterns and/or aneurysms (e.g., based on the 2D matrix described above). For instance, aneurysm detector 500 may be configured to implement a neural network (e.g., a fully connected or convolutional neural network) that may be trained to predict the presence of abnormal strain patterns and/or aneurysms based on the strain maps or the 2D matrix derived therefrom. Aneurysm detector 500 may also be configured to predict the presence of abnormal strain patterns and/or aneurysms based on the strain maps or the 2D matrix using other machine learning techniques such as a random forest based technique.

Aneurysm detector 500 may be configured to indicate the aneurysm assessment results (e.g., aneurysm indications shown in FIG. 5) in various formats. For instance, aneurysm detector 500 may be configured to generate a pattern map (e.g., a strain pattern map or an aneurysm pattern map) to indicate the presence of aneurysms or the likelihood that aneurysms are present in a certain area or region of the heart. The pattern map may be created based on the strain map(s) from which the patterns are determined (e.g., by indicating on the strain map(s) locations or regions at which aneurysms may be presented). The pattern map may be categorical (e.g., binary), where, for example, a value of 1 may indicate aneurysms are present or likely to be present, and a value of 0 may indicate aneurysms are not present or unlikely to be present. The pattern map may also be ordinal (e.g., a ranking indicating the likelihood that aneurysms are present at various locations), or numerical (e.g., where the probability of aneurysms at a location is indicated with a numerical value). The pattern map may be created by color-coding the strain map, where, for example, blue may be used to represent dyskinetic regions (e.g., with a higher probability of containing aneurysms) while red may be used to represent active regions (e.g., with a lower probability of containing aneurysms). In examples, the pattern map may be overlaid with an anatomical image of the heart such as an MR image of the heart to allow an observer (e.g., a medical professional) to visualize the anatomy of the heart and the aneurysms simultaneously. One or both of the pattern map or the anatomical image may be manipulated (e.g., through scaling, rotating, translation, warping, etc.) to align the coordinates of the pattern map with those of the anatomical image. In examples, a user interface may be provided to allow a user to control the aneurysm detection operations. For instance, the user may, through the user interface, define and/or adjust a threshold value for converting a numerical pattern map as described above into a binary pattern map (e.g., numerical values below the threshold may be categorized as having a value of 0, and numerical values above the threshold may be categorized as having a value of 1). As another example, the user may, through the user interface, define a threshold strain value for color-coding the strain map or strain pattern map described herein (e.g., regions with strain values below the threshold may be coded with one color while regions with strain values above the threshold may be coded with another color).

In examples, aneurysm detector 500 may be further configured to covert a strain map or a strain pattern map (e.g., with indications of aneurysms) obtained for one cardiac phase to another cardiac phase. For example, a strain map or strain pattern map may be derived for a first cardiac phase (e.g., which may be any of the standard cardiac phases). To indicate the presence or likelihood of aneurysms for a second cardiac phase such as the end-systolic phase when a myocardium may appear the thickest due to contraction, the coordinates of the heart (e.g., various segments of the heart) in the strain map or strain pattern map may be adjusted to align with the coordinates of the heart at the second cardiac phase such as the strain map or strain pattern map may be converted to match the anatomy of the heart in the second cardiac phase. The alignment or conversion may be performed, for example, based on a dense motion field that may be derived using the techniques described above.

In examples, aneurysm detector 500 may be further configured to calculate the size of an aneurysm (e.g., a potential aneurysm) based on the pattern map described above. For instance, upon identifying an aneurysm location or region in a CMR image, aneurysm detector 500 may determine the total number of pixels enclosed in the region and further determine an area of the region by multiplying the total number of pixels with the spatial resolution of the image. Aneurysm detector 500 may also determine an aneurysm size ratio, which may be defined as the size of the aneurysm(s) over the size of a myocardium (e.g., the myocardium size may be calculated based on a myocardium segmentation). In examples, for each of the locations that is determined to contain an aneurysm, aneurysm detector 500 may be configured to determine a respective segment of the heart (e.g., one of the standard AHA heart segments) to which the aneurysm location belongs, calculate an aneurysm size and a segment size based on respective numbers of pixels associated with the aneurysm location and the segment (e.g., using the technique described above), and further determine whether the segment is an aneurysm segment based on a ratio of the aneurysm size to the segment size. For instance, aneurysm detector 500 may determine that the segment is a normal segment if the ratio of the aneurysm size to the segment size is below a predetermined threshold (e.g., the value of which may be configurable by a user) and that the segment is an aneurysm segment if the ratio of the aneurysm size to the segment size is above the predetermined threshold. Other quantitative metrics may also be determined based on the strain map, strain pattern map, and/or CMR images described herein. For instance, aneurysm detector 500 may be configured to output a value (e.g., a single number with a discrete or continuous value, a binary value, a ranking, etc.) that indicates (e.g., for each patient) whether aneurysm exists and/or the severity of aneurysms.

Figure 6:
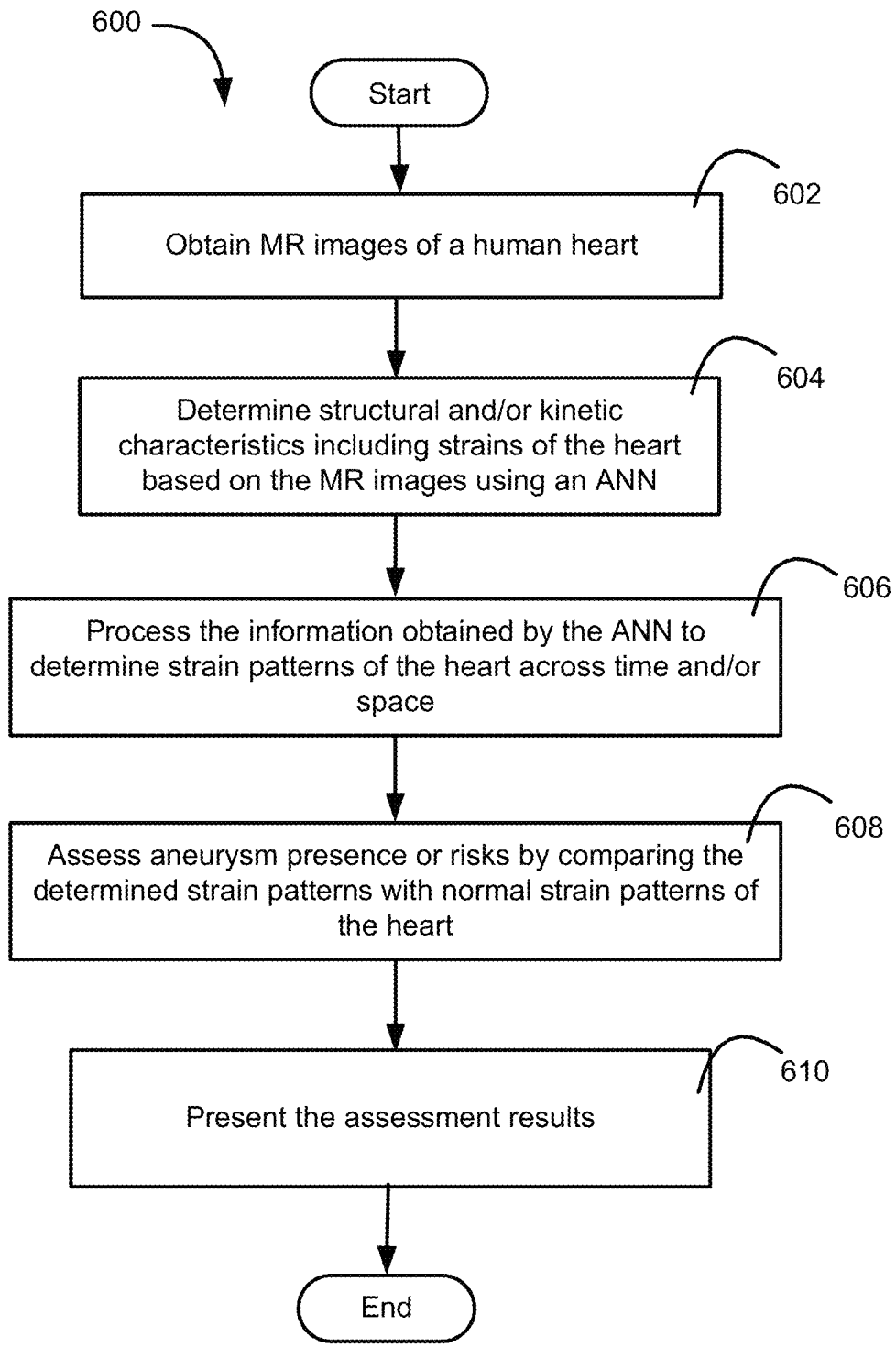
FIG. 6 is a flow diagram illustrating example operations that may be associated with automatic aneurysm detection in accordance with one or more embodiments described herein.

FIG. 6 is a flow diagram illustrating example operations 600 that may be associated with automatic aneurysm detection. As shown, an apparatus configured to perform operations 600 may obtain MR images of a heart at 602. The MR images may be obtained, for example, from a cardiac cine movie and may include short-axis and/or long-axis MR images, 2-chamber MR images, 3-chamber MR images, etc. At 604, the apparatus may determine, using a pre-trained artificial neural network, structural (e.g., thickness of the myocardium) and/or kinetic characteristics (e.g., strains) of the heart based on the MR images and the apparatus may indicate the determined characteristics in a certain format such as through one or more strain maps indicating pixel-wise strain values. At 606, the apparatus may process the information provided by the neural network to determine respective strain patterns associated with one or more locations of the heart. For example, the apparatus may rearrange the strain values into an alternative form of representation such as a multi-dimensional matrix that depicts the distribution of the strain values across time (e.g., cardiac phases) and/or space (e.g., pixel locations of various anatomical components of the heart). The apparatus may then analyze the information included in the multi-dimensional matrix, for example, via PCA, temporal and/or spatial averaging, and/or other types of suitable data analysis techniques (e.g., singular value decomposition, random forest, support vector machine, deep learning, etc.) to determine the strain patterns indicated by the information included in the matrix.

At 608, the apparatus may compare the strain patterns determined at 606 with predetermined normal strain patterns of the heart to whether an area or region of the heart is an aneurysm site or has a high probability of being an aneurysm site. For example, if the normal strain pattern shows that the strains at a location decrease in a first cardiac phase and increase in a second cardiac phase, but the determined pattern shows that the strain values change in a different (e.g., opposite) manner, the apparatus may determine that the location is an aneurysm site (e.g., having a high risk or probability of containing an aneurysms). At 610, the apparatus may present the results of the aneurysm assessment. For example, the apparatus may indicate the results by color-coding a strain map or strain pattern map to present the aneurysm sites in one color and the normal sites in another color. The apparatus may also overlay the color-coded map on top of an anatomical image (e.g., an MR image) of the heart so as to an observer may visualize the aneurysms and the anatomy of the heart simultaneously.

Figure 7:
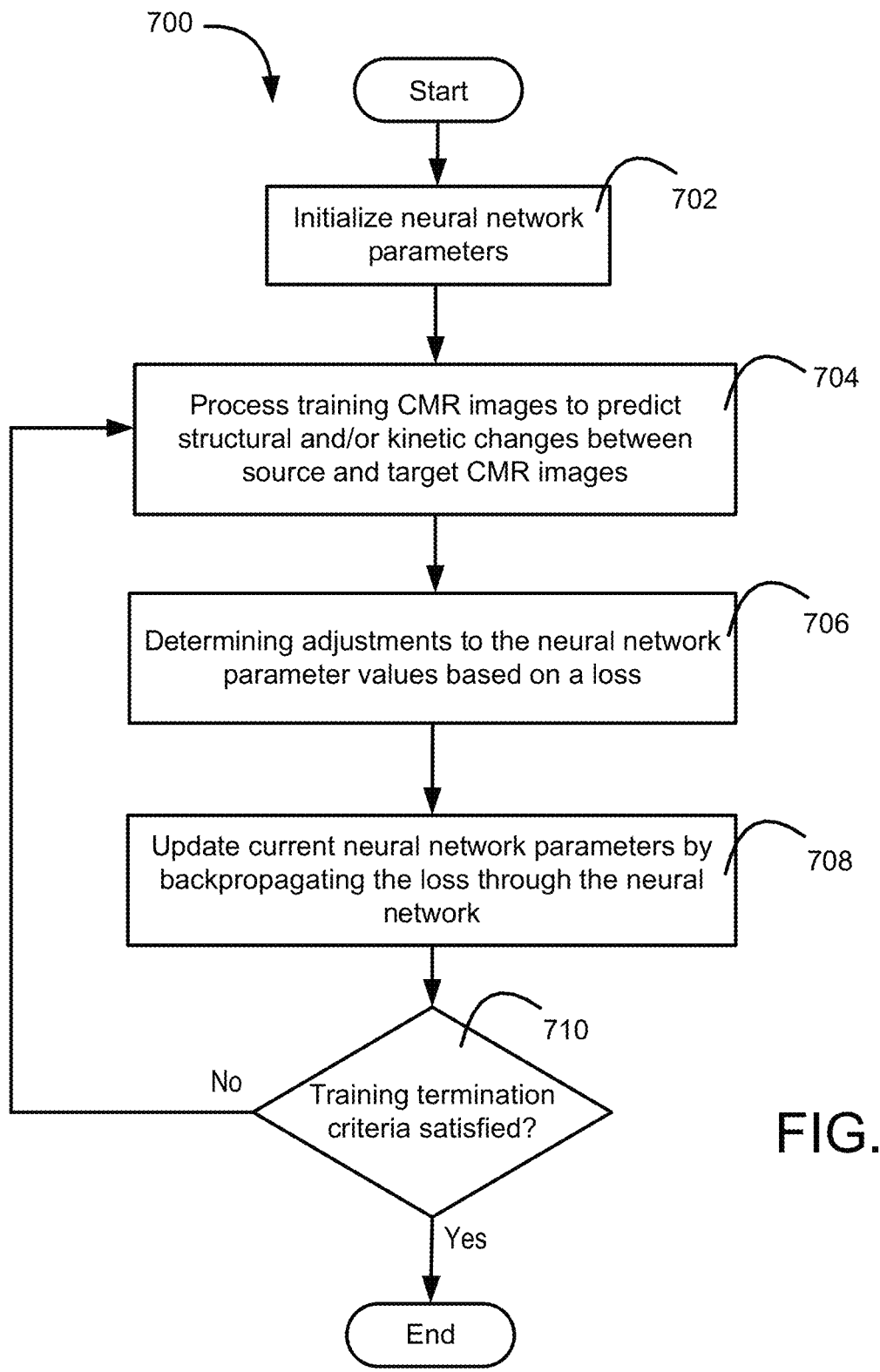
FIG. 7 is a flow diagram illustrating example operations that may be associated with the training of an artificial neural network in accordance with one or more embodiments described herein.

FIG. 7 is a flow diagram illustrating example operations 700 that may be performed to train one or more of the artificial neural networks described herein, for example, for determining a motion field based on CMR images of a heart, from which strains of the heart may be calculated. As shown, the operations may include initializing the parameters of the neural network (e.g., weights associated with one or more layers of the neural network) at 702. For example, the parameters of the neural network may be initialized based on samples from one or more probability distributions or parameter values of another neural network with a similar architecture. The operations may further include receiving and processing, at the neural network, training CMR images (e.g., from a cardiac cine movie) at 704 to predict a motion field that may indicate structural and/or kinetic changes of the heart from a source CMR image to a target CMR image. A loss associated with the predicted changes may then be assessed at 706, based which adjustments to the neural network parameters may be determined, for example, based on a gradient descent of the loss. The loss may be calculated using various techniques. As an example, the loss may be determined by warping the source CMR image based on the motion field (e.g., by applying spatial transform to the source CMR image), comparing the warped CRM image with the target CMR image, and calculating a difference between the two CRM images based on mean squared errors, an L1 norm, an L2 norm, etc. Based on the loss and the network parameter adjustments determined therefrom, current neural network parameters may be updated at 708, for example, by backpropagating the loss (e.g., the gradient descent of the loss) through the neural network. Subsequently, a determination may be made at 710 regarding whether one or more training termination criteria are satisfied. For example, the training termination criteria may be satisfied if a pre-determined number of training iterations has been completed, or if the change in the prediction loss between two training iterations falls below a predetermined threshold. If the determination at 710 is that the training termination criteria are not satisfied, the training may return to 704. If the determination at 710 is that the training termination criteria are satisfied, the training may end.

Figure 8:
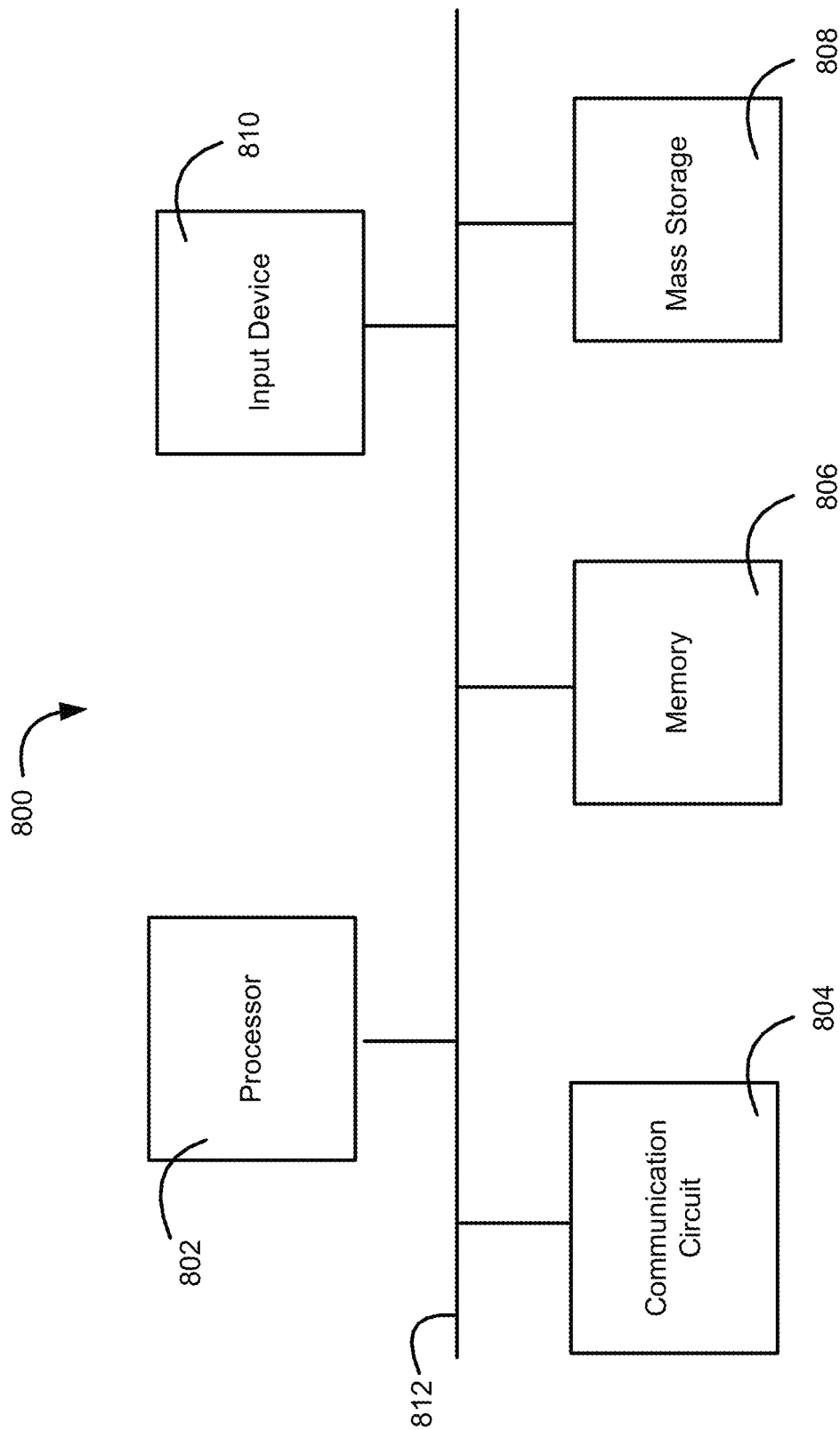
FIG. 8 is a block diagram illustrating components of an example apparatus that may be configured to perform the tasks described herein.

The automatic aneurysm assessment system or apparatus described herein (e.g., aneurysm assessment system 100 of FIG. 1, aneurysm assessment system 200 of FIG. 2, etc.) may be implemented using one or more processors, one or more storage devices, and/or other suitable accessory devices such as display devices, communication devices, input/output devices, etc. FIG. 8 is a block diagram illustrating an example apparatus 800 that may be configured to perform one or more of the tasks described herein. As shown, apparatus 800 may include a processor (e.g., one or more processors) 802, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. Apparatus 800 may further include a communication circuit 804, a memory 806, a mass storage device 808, an input device 810, and/or a communication link 812 (e.g., a communication bus) over which the one or more components shown in FIG. 8 may exchange information. The communication circuit 804 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 806 may include a storage medium configured to store machine-readable instructions that, when executed, cause the processor 802 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 808 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 802. The input device 810 may include a keyboard, a mouse, a voice-controlled input device, a touch sensitive input device (e.g., a touch screen), and/or the like for receiving user inputs to apparatus 800.

It should be noted that apparatus 800 may operate as a standalone device or may be connected (e.g., networked, clustered, etc.) with other computation devices to perform the functions described herein. And even though only one instance of each component is shown in FIG. 8, a skilled person in the art will understand that apparatus 800 may include multiple instances of one or more of the components shown in the figure. Furthermore, although the examples are described herein with reference to various types of neural networks, various types of layers, and/or various tasks being performed by certain types of neural networks or layers, those references are made merely for illustration purposes and not meant to limit the scope of the disclosure. In addition, the operation of apparatus 800 is depicted and described herein with a specific order. It should be appreciated, however, that these operations may occur in various orders, concurrently, and/or with other operations not presented or described herein. And not all operations that apparatus 800 is capable of performing are depicted and described herein, and not all illustrated operations are required to be performed by the apparatus.

For simplicity of explanation, the operation of the example apparatus or systems is depicted and described herein with a specific order. It should be appreciated, however, that these operations may occur in various orders, concurrently, and/or with other operations not presented or described herein. Furthermore, it should be noted that not all operations that a system or apparatus is capable of performing are depicted and described herein, and not all illustrated operations are required to be performed by the system or apparatus.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. An apparatus, comprising:
one or more processors configured to:
obtain strain values associated one or more locations of a human heart and one or more cardiac phases of the human heart;
derive a representation of the strain values across the one or more locations and the one or more cardiac phases, wherein the representation includes a two-dimensional (2D) matrix, a first dimension of the 2D matrix encompasses the one or more cardiac phases of the human heart, and a second dimension of the 2D matrix encompasses the one or more locations of the human heart;
determine, based on the derived representation of the strain values, respective strain patterns associated with the one or more locations of the human heart, wherein the strain patterns are determined from the 2D matrix using at least one of a principal component analysis (PCA) technique or a machine learning technique; and
determine, based on the determined strain patterns, whether the one or more locations are aneurysm locations.

2. The apparatus of claim 1, wherein the one or more processors being configured to obtain the strain values associated the one or more locations of the human heart and the one or more cardiac phases of the human heart comprises the one or more processors being configured to obtain one or more strain maps that represent the strain values.

3. The apparatus of claim 1, wherein the one or more processors being configured to obtain the strain values comprises the one or more processors being configured to determine the strain values or receive the strain values from another apparatus.

4. The apparatus of claim 1, wherein the one or more processors being configured to determine whether the one or more locations are aneurysm locations comprises the one or more processors being configured to compare the respective strain patterns associated with the one or more locations of the human heart with corresponding predetermined normal strain patterns associated with the one or more locations of the human heart and provide an indication of whether the one or more locations are aneurysm locations based on the comparison.

5. The apparatus of claim 1, wherein the respective strain patterns associated with the one or more locations of the human heart include respective average strain values at the one or more locations of the human heart across the one or more cardiac phases, and wherein the one or more processors being configured to determine whether the one or more locations are aneurysm locations comprises the one or more processors being configured to compare the respective average strain values at the one or more locations of the human heart with predetermined normal average strain values for the one or more locations of the human heart and provide an indication of whether the one or more locations are aneurysm locations based on the comparison.

6. The apparatus of claim 1, wherein, for each of the one or more locations that is determined to be an aneurysm location, the one or more processors are further configured to determine a respective segment of the human heart to which the aneurysm location belongs, determine an aneurysm size based on a number of pixels associated with the aneurysm location, determine a segment size based on a number of pixels associated with the segment, and determine whether the segment is an aneurysm segment based on a ratio of the aneurysm size to the segment size.

7. The apparatus of claim 6, wherein the one or more processors being configured to determine whether the segment is the aneurysm segment comprises the one or more processors being configured to compare the ratio of the aneurysm size to the segment size with a configurable threshold and determine whether the segment is the aneurysm segment based on the comparison.

8. The apparatus of claim 1, wherein, for each of the one or more locations that is determined to be an aneurysm location, the one or more processors are further configured to indicate the aneurysm location on a strain map and overlay the strain map with a cardiac magnetic resonance (CMR) image of the human heart so as to indicate the aneurysm location with respect to an anatomy of the human heart.

9. The apparatus of claim 8, wherein the strain map is associated with a first cardiac phase, the CMR image is associated with a second cardiac phase, and the one or more processors being configured to overlay the strain map with the CMR image comprises the one or more processors being configured to adjust the strain map such that coordinates of the human heart in the strain map are aligned with coordinates of the human heart in the CMR image.

10. A method of automatic aneurysm assessment, comprising:
obtaining strain values associated with one or more locations of a human heart and one or more cardiac phases of the human heart;
deriving a representation of the strain values across the one or more locations and the one or more cardiac phases, wherein the representation includes a two-dimensional (2D) matrix, a first dimension of the 2D matrix encompasses the one or more cardiac phases of the human heart, and a second dimension of the 2D matrix encompasses the one or more locations of the human heart;
determining, based on the derived representation of the strain values, respective strain patterns associated with the one or more locations of the human heart, wherein the strain patterns are determined from the 2D matrix using at least one of a principal component analysis (PCA) technique or a machine learning technique; and
determining, based on the determined strain patterns, whether the one or more locations are aneurysm locations.

11. The method of claim 10, wherein obtaining the strain values associated the one or more locations of the human heart and the one or more cardiac phases of the human heart comprises obtaining one or more strain maps that represent the strain values.

12. The method of claim 10, wherein obtaining the strain values comprises determining the strain values based on cardiac magnetic resonance (CRM) images of the human heart using an artificial neural network or receiving the strain values from another apparatus.

13. The method of claim 10, wherein determining whether the one or more locations are aneurysm locations comprises comparing the respective strain patterns associated with the one or more locations of the human heart with corresponding predetermined normal strain patterns associated with the one or more locations of the human heart and providing an indication of whether the one or more locations are aneurysm locations based on the comparison.

14. The method of claim 10, wherein the respective strain patterns associated with the one or more locations of the human heart include respective average strain values at the one or more locations of the human heart across the one or more cardiac phases, and wherein determining whether the one or more locations are aneurysm locations comprises comparing the respective average strain values at the one or more locations of the human heart with predetermined normal average strain values for the one or more locations of the human heart and providing an indication of whether the one or more locations are aneurysm locations based on the comparison.

15. The method of claim 10, further comprising, for each of the one or more locations that is determined to be an aneurysm location, determining a respective segment of the human heart to which the aneurysm location belongs, determining an aneurysm size based on a number of pixels associated with the aneurysm location, determining a segment size based on a number of pixels associated with the segment, and determining whether the segment is an aneurysm segment based on a ratio of the aneurysm size to the segment size.

16. The method of claim 10, further comprising, for each of the one or more locations that is determined to be an aneurysm location, indicating the aneurysm location on a strain map and overlaying the strain map with a cardiac magnetic resonance (CMR) image of the human heart so as to indicate the aneurysm location with respect to an anatomy of the human heart.

* * * * *